United States Patent [19]

Rall et al.

[11] Patent Number: 5,746,212
[45] Date of Patent: May 5, 1998

[54] PROCESS AND DEVICE FOR MEASURING VITAL FETAL PARAMETERS DURING LABOR AND DELIVERY

[76] Inventors: Gerhard Rall, Bozzaristr. 39f., D-8000 Munchen 90; Reinhold Knitza, Bergstr. 3, D-8015 Gauting, both of Germany

[21] Appl. No.: 307,647
[22] PCT Filed: Mar. 19, 1993
[86] PCT No.: PCT/EP93/00664
§ 371 Date: Apr. 21, 1995
§ 102(e) Date: Apr. 21, 1995
[87] PCT Pub. No.: WO93/18705
PCT Pub. Date: Sep. 30, 1993

[30] Foreign Application Priority Data

Mar. 20, 1992 [DE] Germany ............ 42 09 147.0

[51] Int. Cl.[6] ......................................... A61B 5/04
[52] U.S. Cl. ...................... 128/672; 128/687; 128/677; 128/748
[58] Field of Search .................... 128/668, 672, 128/677, 775, 778, 673, 748, 675

[56] References Cited

U.S. PATENT DOCUMENTS

| | | | |
|---|---|---|---|
| 4,476,871 | 10/1984 | Hon | 128/778 |
| 4,798,588 | 1/1989 | Aillon | 128/673 |
| 4,944,307 | 7/1990 | Hon et al. | 128/748 |
| 5,050,613 | 9/1991 | Newman et al. | 128/691 |
| 5,184,619 | 2/1993 | Austin | 128/778 |
| 5,205,296 | 4/1993 | Dukes et al. | 128/775 |
| 5,279,308 | 1/1994 | DiSabito et al. | 128/775 |
| 5,373,852 | 12/1994 | Harrison et al. | 128/778 |

FOREIGN PATENT DOCUMENTS

| | | | |
|---|---|---|---|
| 0097454 | 1/1984 | European Pat. Off. | 128/775 |
| 0135840 | 4/1985 | European Pat. Off. | 128/635 |
| PS-3810008 | 10/1989 | Germany | |
| WO90/01293 | 2/1990 | WIPO | |

*Primary Examiner*—Robert L. Nasser
*Attorney, Agent, or Firm*—Burns, Doane, Swecker & Mathis, L.L.P.

[57] ABSTRACT

A process for measuring vital, fetal parameters during parturition. It is essential in this process that the blood pressure of the fetus is discontinuously measured in the arterial system by carrying out the occlusion process using the annular uterine tissue and the presenting part of the fetus and a pressure sensor and a sensor sensing the blood flow characteristics.

27 Claims, 5 Drawing Sheets

FIG.1
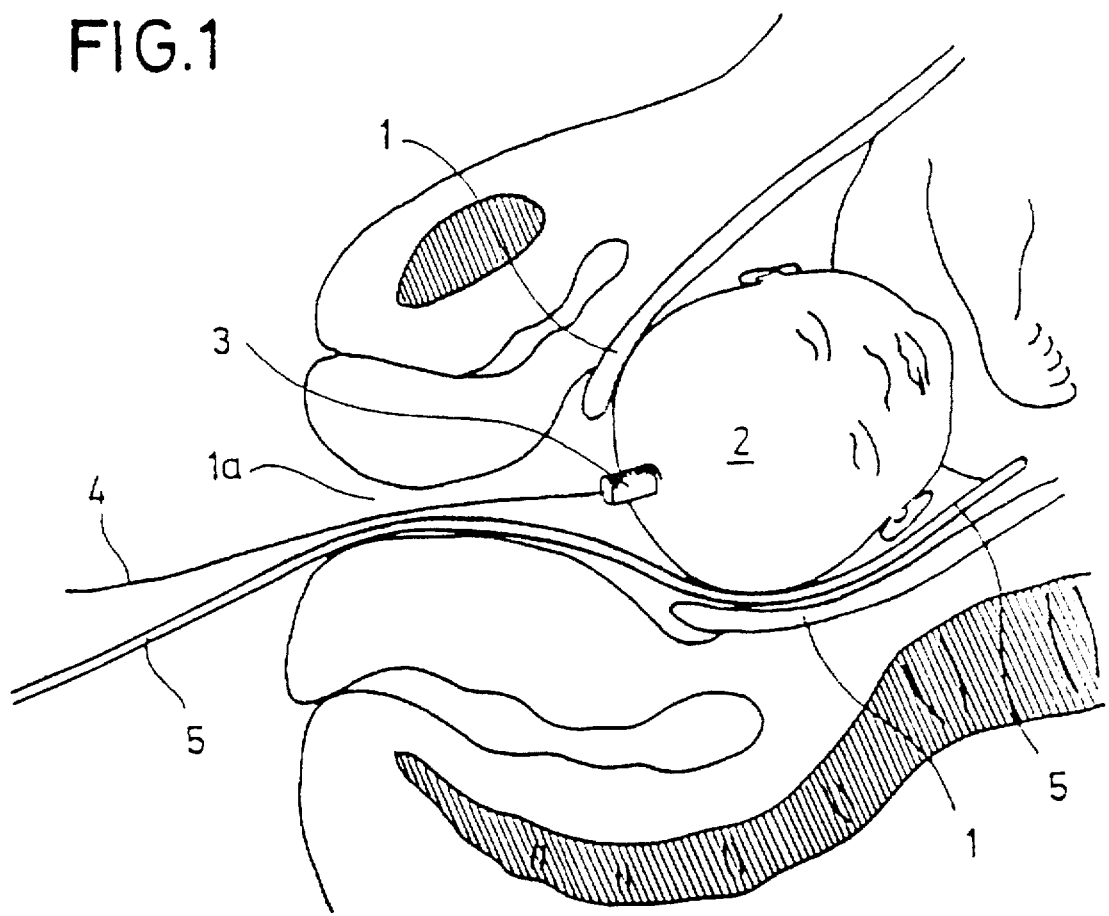
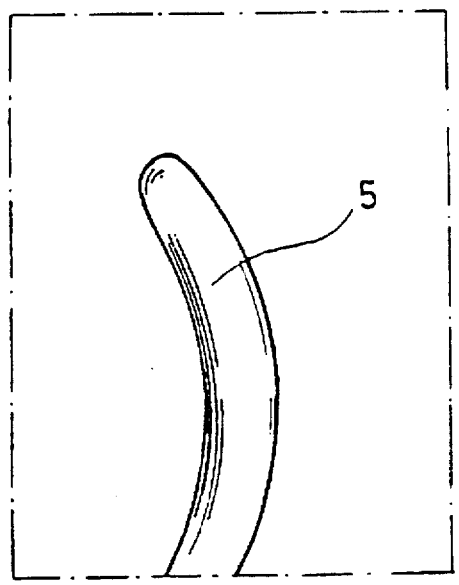
FIG.1a

FIG.2
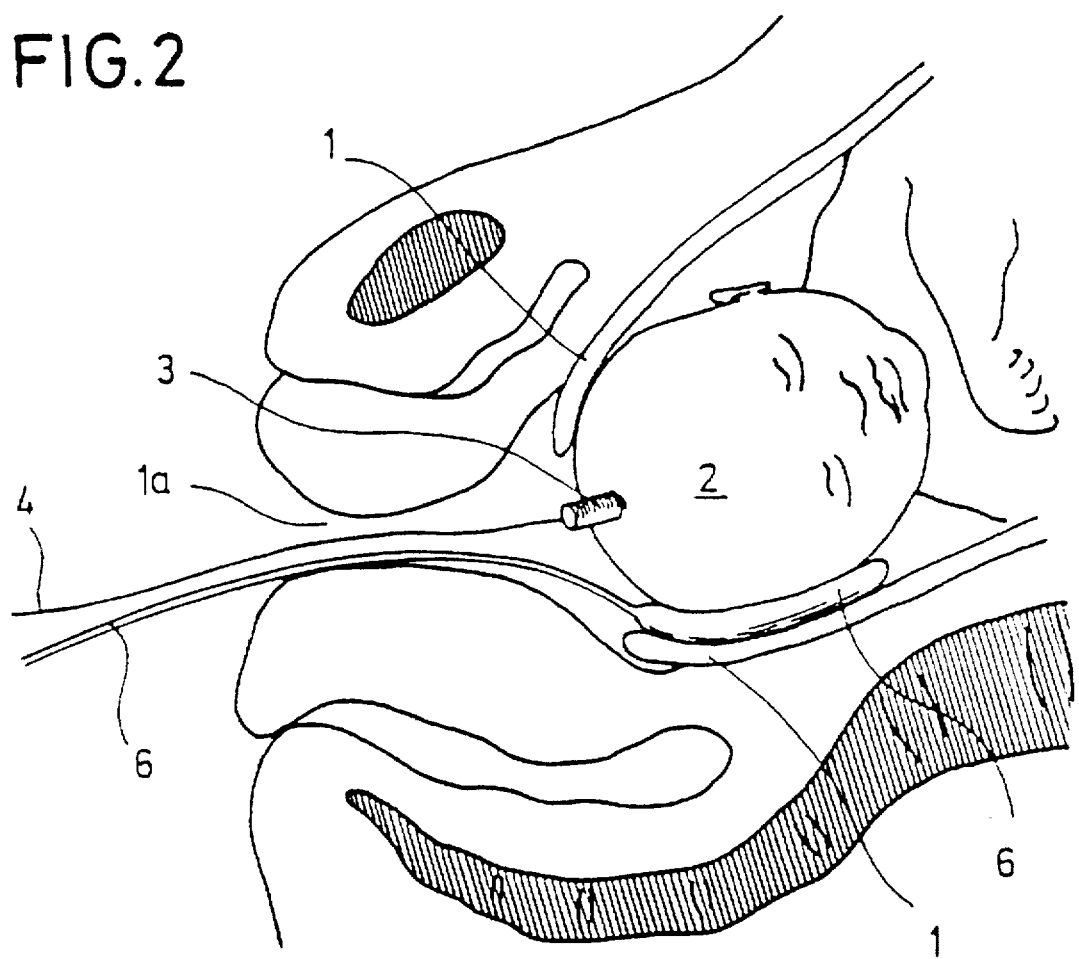
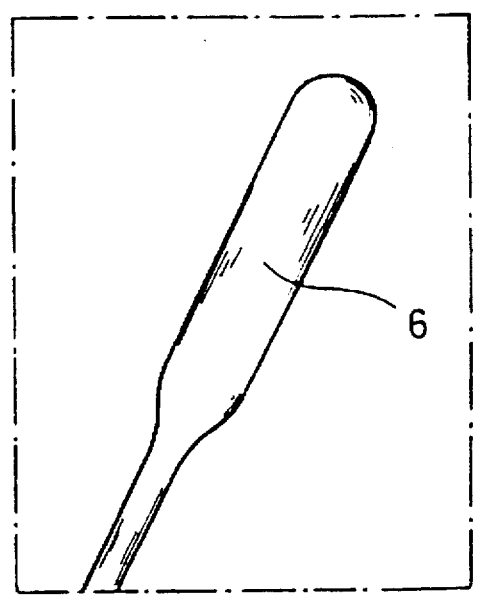
FIG.2a

FIG.3
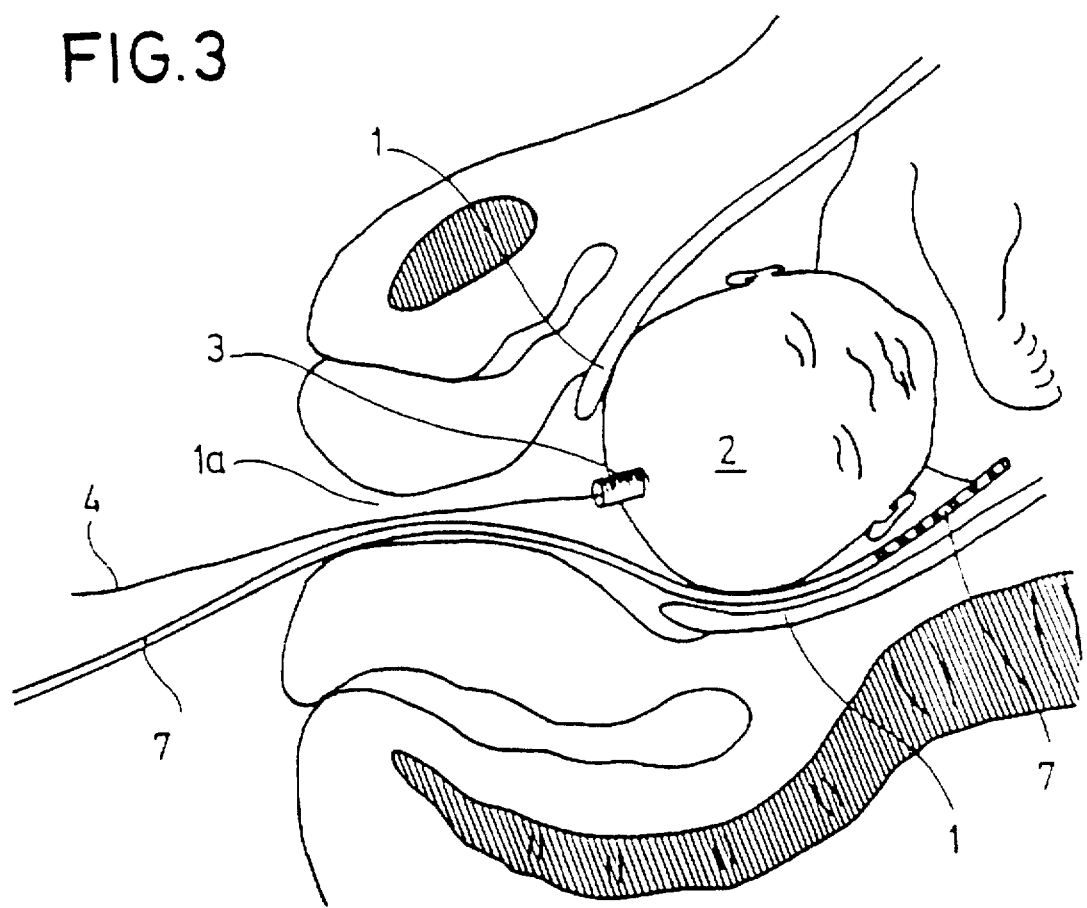
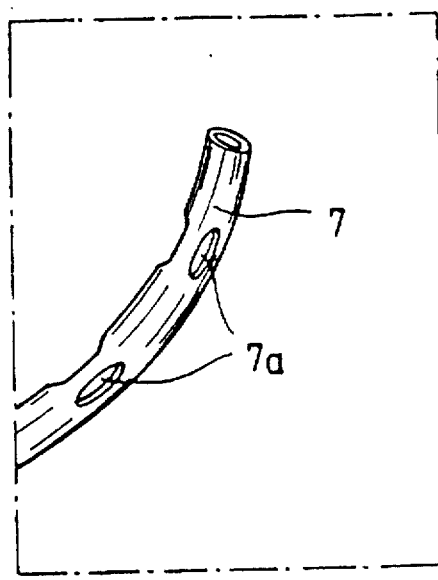
FIG.3a

FIG. 5
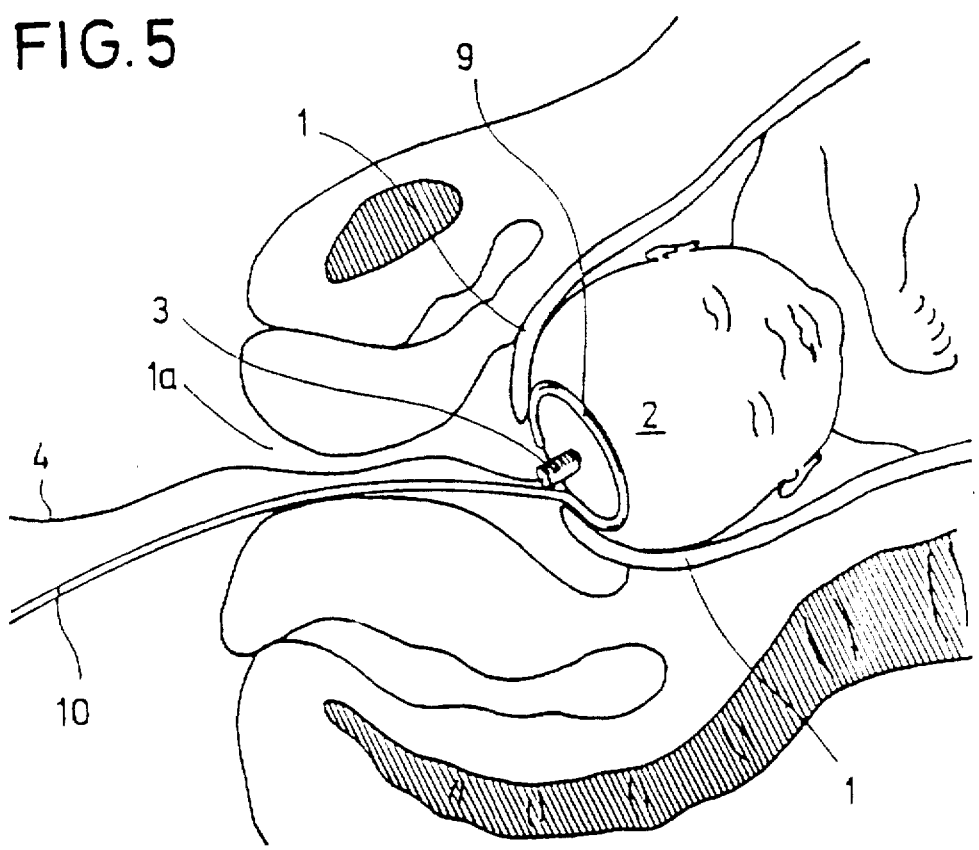
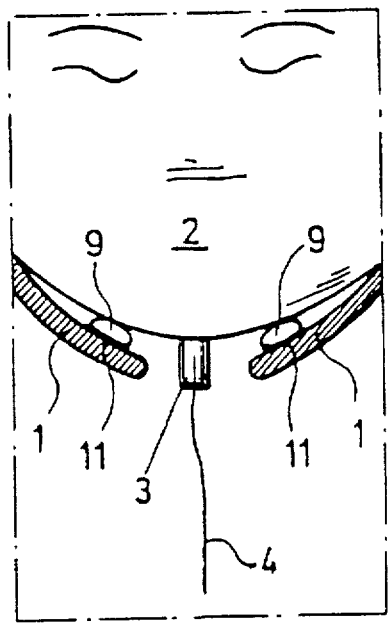
FIG. 5a
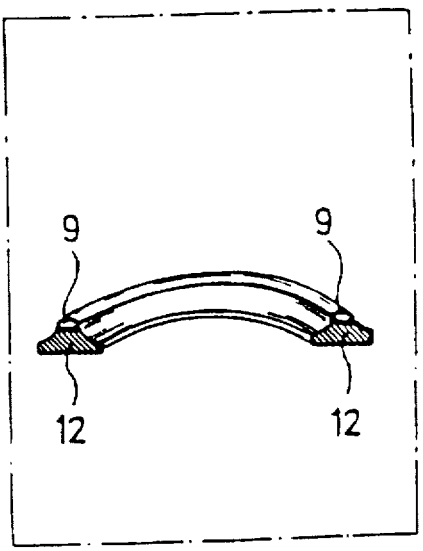
FIG. 5b

PROCESS AND DEVICE FOR MEASURING VITAL FETAL PARAMETERS DURING LABOR AND DELIVERY

FIELD OF THE INVENTION

The invention relates to a process and a device for measuring vital fetal parameters during labor and delivery.

BACKGROUND OF THE INVENTION

So far, a device for carrying out the so-called cardiotocography (CTG) has mainly been used in practice in obstetrics.

The child's heart rate and the mother's labor are represented in two recording tracks in a side-by-side relationship on a recording strip with this device so that, e.g., a midwife can watch the parturition by means of these recordings.

However, the CTG process does not supply any direct parameters. The recordings must rather be interpreted by the midwife who consults a doctor when she is in doubt.

It is the object of the invention to provide a process and a device which supply absolute values of vital fetal parameters during parturition so that midwives get measuring values with clear statements.

In order to attain this object the invention provides that the blood pressure of the fetus is discontinuously measured in the arterial system by carrying out the occlusion process by means of the annular uterine tissue and the presenting part of the fetus and a pressure sensor and a sensor sensing the blood flow characteristics.

Thus, the invention uses the principle of occlusion measurement of the blood pressure.

Although this principle has been generally known for a long time, experts have not recognized that, due to a further development, this principle can surprisingly also be used for an indirect measurement of the blood pressure of the fetus during parturition.

In the known occlusion process for the indirect and discontinuous measuring of the blood pressure of a person, a cuff is placed around the upper arm. The cuff is inflated sufficiently with an air pump at the beginning of the measuring of blood pressure that all blood vessels collapse under the pressure of the cuff and there is no longer any blood flow. Then the air is slowly discharged from the cuff, the blood pressure range being slowly swept. As soon as the cuff pressure has slightly dropped below the systolic blood pressure, blood can again flow in the veins during the time of the highest arterial blood pressure of the systoles.

Since the veins are still largely compressed, a hissing noise is produced in the veins beyond the cuff during the short moment during which arterial blood flows into the arm, which can be auscultated by means of a stethoscope (Korotkow sounds).

The noise can also be detected, of course, by a microphone and can be evaluated, e.g., electronically.

During the further course of the measuring, the cuff pressure is continuously lowered. Korotkow sounds get louder and louder, but then softer gain. If the cuff pressure drops finally below the diastolic blood pressure, Korotkow sounds disappear completely.

The cuff pressure at which this noise occurs for the first time corresponds to the systolic blood pressure. The cuff pressure at which this noise disappears finally or clearly decreases in terms of intensity corresponds to the diastolic blood pressure.

SUMMARY OF THE INVENTION

In the process according to the invention the annular uterine tissue is directly or indirectly used for occlusion measuring in a surprising manner.

The process according to the invention is designed so that the annular uterine tissue is used as an occlusion cuff with respect to the presenting part of the infant during the maximum of a contraction (peak of contraction), the occlusion pressure (pressure in the cuff higher than the systolic arterial blood pressure of the fetus) between the uterine tissue and the presenting part of the infant being ascertained by a pressure sensor and a sensor sensing the blood flow characteristics, the systolic and the diastolic arterial blood pressure of the infant being determined as the contraction subsides.

If the contraction is strong enough, the blood flow is completely cut off in the relevant part of the fetus during the peak of a contraction. As the contraction subsides, the systolic and the diastolic blood pressure of the fetus can then be determined successively.

If the labor is not that intensive, the midwife can cause the necessary occlusion pressure by pressing on the abdomen or the uterus of the mother. In many cases it may be sufficient to ask the mother to press by means of the abdominal muscles.

However, according to a further embodiment of the process according to the invention, the uterine tissue can also be used by disposing an elastic hollow ring filled with a fluid between the uterine tissue and the presenting part. The hollow ring is inflated until the occlusion pressure is reached, the systolic and the diastolic blood pressure of the infant being determined during the decrease of the pressure in the hollow ring by the pressure sensor and the sensor sensing the blood flow characteristics.

During a relatively mild labor, the hollow ring can be additionally inflated in order to reach the necessary occlusion pressure so that the occluding pressure reaches the systolic pressure of the fetus.

However, such a measuring of the fetal blood pressure in the arterial vascular system can also be carried out by the inflatable hollow ring independently of the labor.

According to the invention, the fetal ECO can be derived from an electrode attachable to the fetus. The obtained signals can also facilitate recognition of the blood flow characteristics.

The process of the invention can also be combined with the CTG process and/or the ECG process and/or the process of hemoglobinometry, i.e., preferably with the process of pulse oximetry, but also with the measuring of dyshemoglobins and the absolute hemoglobin value.

The process of the present invention can also include the step of deriving the fetal ECG from a sensor such as the sensor sensing the blood flow characteristic or from the pressure sensor.

A device for carrying out the process is provided according to the invention. The device carries out the occlusion process and consists of a sensor disposed on the presenting part of the fetus, which senses the blood flow characteristics, and a pressure sensor disposed between the uterine tissue and the fetus.

Suitable sensors reacting to blood flow characteristics are known, e.g., the corresponding sensors as parts of the devices according to EP 84 110 306 or the international publication WO 90/01293 or DE-PS 38 10 008.

The device according to the present invention may further include electrical contacts for deriving the fetal ECG. The electrical contacts are provided on the blood flow sensor or the pressure sensor.

Doppler effect sensors or piezofoil sensors, for example, can also be used for this purpose.

The pressure sensor may consist of a hose filled with a fluid and closed at the front end, at whose rear end a pressure sensor element is disposed.

However, the pressure sensor can also be designed as a balloon catheter or as an intrauterine pressure probe or as a double-recurrent balloon catheter sensing both the occlusion pressure and simultaneously also the intrauterine pressure.

The device can also consist of a sensor disposed on the presenting part of the fetus and sensing the blood flow characteristics and of a pressure sensor disposed between the annular uterine tissue and the presenting part of the fetus, which is designed as an elastic, inflatable hollow ring filled with a fluid.

According to the invention, the hollow ring and the sensor sensing the blood flow characteristics can be fixed against each other as a constructional unit.

In this fashion they cannot be displaced against each other, if, e.g., the fetal head rotates away within the uterus after the application of the is arrangement.

BRIEF DESCRIPTION OF THE DRAWING

Further features and advantages of the invention will be understood from the following description in connection with the drawing, in which:

FIG. 1 & 1a show schematically a first example of a device for carrying out the process, FIG. 2 shows another device of this kind, FIG. 2a shows a detail of FIG. 2, FIG. 3 shows another example of such a device, FIG. 3a shows a detail of FIG. 3, FIG. 5 shows still another example of such a device, FIG. 5a shows a detail of FIG. 5, and FIG. 5b shows a further detail of FIG. 5a.

FIGS. 3a, 4a, 5a and, 5b are drawn in enlarged scale.

DETAILED DESCRIPTION OF THE INVENTION

Figure 4:
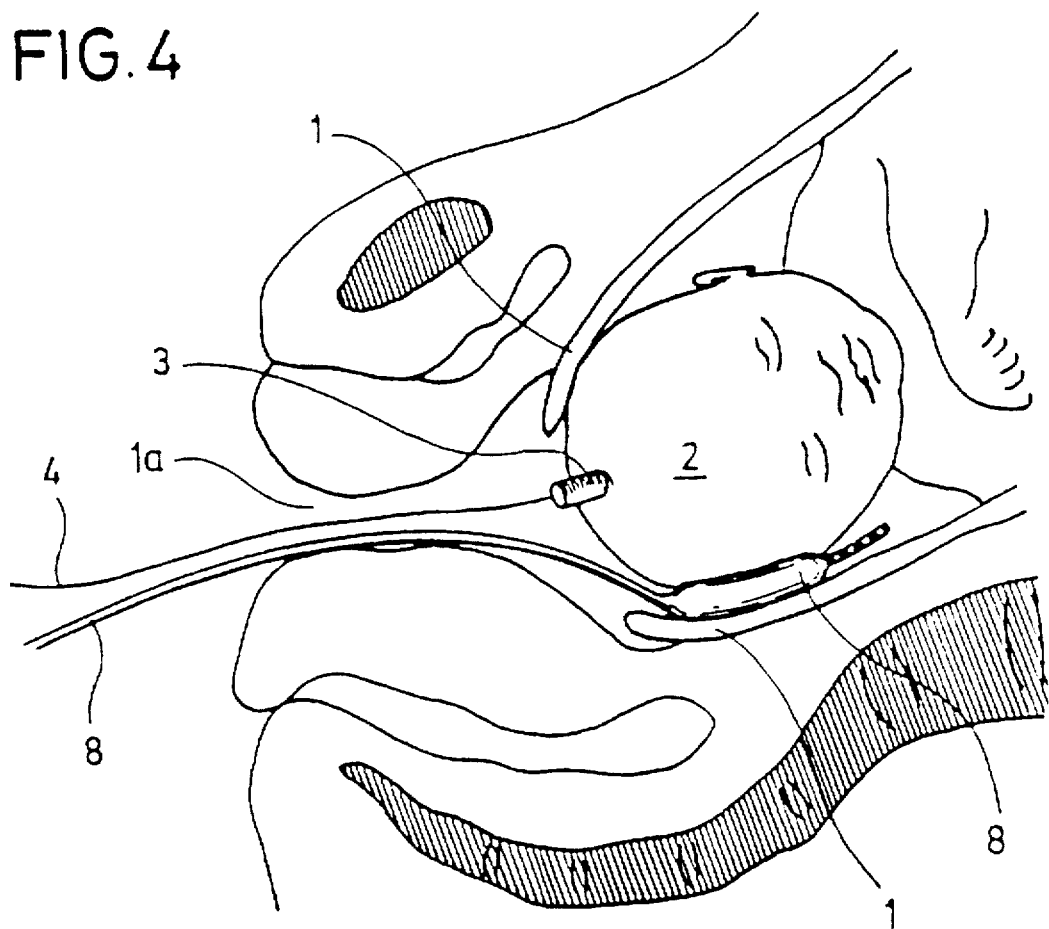
FIG. 4 shows another device of this kind.

The uterine tissue, called cervical os in the following for the sake of simplification, is designated with 1 in the examples of embodiments and the vagina is designated with 1a.

During parturition the fetal head 2 is pressed against the cervical os 1.

An element 3 is affixed to the fetal head 2 through the vagina 1a, which is a part of the blood flow sensor 4 sensing fetal blood flow characteristics. The element can be a spiral already used for this purpose, but also a known piezofoil.

The blood flow sensor 4 supplies corresponding signals to an evaluating unit (not shown).

In order to be able to detect the pressure prevailing between the cervical os and having an occluding effect, a further device is still provided.

This device is represented by a hose 5 in the example according to FIG. 1, which is inserted between the cervical os 1 and the head 2 of the child.

The hose 5 is closed at the front end and filled with a fluid which transmits the pressure to be measured to the rear end of the hose 5, to which a pressure sensor element is affixed.

In the example according to FIG. 2, a balloon catheter 6 is introduced into the occlusion zone as a sensor for sensing the occlusion pressure.

A further possible embodiment of the sensor for occlusion pressure sensing is the use of an already clinically introduced intrauterine pressure probe 7. Any differences between the intrauterine pressure and the occlusion pressure can be balanced via a conversion factor (FIG. 3).

According to FIG. 3a, openings 7a are provided on the circumference at the catheter tip of the intrauterine pressure probe.

A sensor for sensing the occlusion pressure is designed as a double-recurrent balloon catheter 8. (The hose of the catheter has two separate channels or lumina, the one channel being connected to the balloon of the catheter, the other one to the catheter tip). The balloon catheter can be used both for occlusion pressure detection and for the simultaneous measuring of the intrauterine pressure.

Figure 4A:
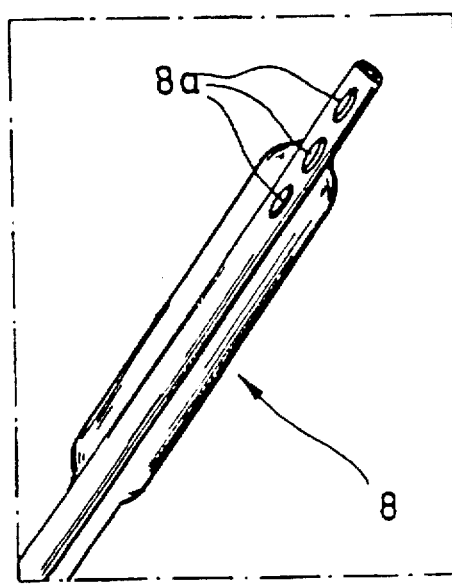
FIG. 4a shows a detail of FIG. 4.

Such a double-recurrent balloon catheter with openings laterally disposed on the catheter tip is schematically shown in FIG. 4a. If the fetal blood pressure is to be measured in the arterial vascular system in the case of relatively mild contractions or between contractions, the device according to FIG. 5 can achieve this purpose in order to also reach a sufficient occlusion pressure.

For this purpose, an elastic hollow ring 9 filled with a fluid is inserted around the blood flow sensor element 3 between the head 2 of the fetus and the uterine tissue 1. The hollow ring 9 can be inflated by means of a hose 10, and the pressure prevailing in its interior can also be measured. Thus, the occlusion pressure can also be reached by additionally inflating the hollow ring 9 in the case of a relatively mild contraction. A sufficient occlusion pressure can also be reached between the contractions by means of the hollow ring 9. The hollow ring 9 is flattened on one side, this side 11 being relatively hard and serves as a support with respect to the uterine tissue 1.

In the example according to FIG. 5b, the hollow ring 9 is mounted on a flat support ring 12, which is made of a sufficiently firm, but flexible material and is supported on the uterine tissue 1. The support surface of the hollow ring 9 on the head 2 of the child is smaller than the support surface of the support ring 12.

Thus, an increase in pressure can be achieved in a simple fashion. The presenting part of the fetus may not always be the head. The breech of the child can also be accommodated. The measurement of the fetal blood pressure in the arterial vascular system is possible here, as well.

The hollow ring 9 and the support ring 12 can also extend to less than 360 degrees.

The process can also be carried out prior to parturition, e.g., after a premature rupture and independently of labor.

The systolic and diastolic fetal blood pressure can also be measured in reverse order during the increase of a contraction. As a contraction subsides, the measuring can be repeated in the customary order so that more accurate values are achieved (double determination).

We claim:

1. A process for measuring the vital parameters of a fetus inside the uterus of a mother during labor and delivery, said process comprising:

forming an occlusion cuff about the presenting part of the fetus;

disposing a blood flow sensor on the presenting part of the fetus;

measuring the blood flow in the presenting part of the fetus through said blood flow sensor;

disposing a pressure sensor between the annular uterine tissue and the presenting part of the fetus;

discontinuously measuring the occlusion pressure between the annular uterine tissue and the presenting part of the fetus through said pressure sensor; and determining the systolic and diastolic arterial blood pressure of the fetus.

2. A process according to claim 1 including measuring the occlusion pressure at the peak of a uterine contraction, and determining the systolic and the diastolic arterial blood pressure of the fetus as the contraction subsides.

3. A process according to claim 1 further comprising the step of determining the fetal ECG through one of said blood flow sensor and said pressure sensor.

4. A process according to claim 1 further comprising the step of simultaneously measuring at least one of the fetal homoglobinometry, the fetal pulse oximetry, and the cardiotocography.

5. A process according to claim 1 further comprising the step of pressing on the uterus to enhance the forming of the occlusion cuff.

6. A process according to claim 1 further comprising the step of having the mother press by using her abdominal muscles to enhance the forming of the occlusion cuff.

7. A process according to claim 1 wherein said pressure sensor is an elastic hollow ring filled with fluid, the step of measuring the occlusion pressure including inflating said elastic hollow ring, and the step of determining the systolic and diastolic arterial blood pressure of the fetus including decreasing the pressure in said elastic hollow ring.

8. A process according to claim 7 further comprising the step of determining the fetal ECG through one of said blood flow sensor and said pressure sensor.

9. A process according to claim 7 further comprising the step of simultaneously measuring at least one of the fetal homoglobinometry, the fetal pulse oximetry, and the cardiotocography.

10. A device for measuring the vital parameters of a fetus inside the uterus of a mother during labor and delivery comprising:

a blood flow sensor for placement on a presenting part of the fetus and adapted to measure the blood flow in a presenting part of the fetus;

a pressure sensor for placement between annular uterine tissue and the presenting part of the fetus and adapted to measure discontinuously an occlusion pressure between the annular uterine tissue and the presenting part of the fetus; and means for determining a systolic and diastolic pressure of the fetus based on the occlusion pressure.

11. A device according to claim 10 wherein said blood flow sensor and said pressure sensor are fixed against each other.

12. A device according to claim 10 wherein said pressure sensor includes a hose having a closed front end and a rear end, said hose filled with fluid, and a pressure sensor element affixed to said rear end of said hose.

13. A device according to claim 10 wherein said pressure sensor is a balloon catheter.

14. A device according to claim 10 wherein said pressure sensor is an intrauterine pressure probe.

15. A device according to claim 10 wherein said pressure sensor is a double-recurrent balloon catheter adapted to simultaneously measure the occlusion pressure and the intrauterine pressure.

16. A device according to claim 10 wherein said pressure sensor is an elastic, inflatable hollow ring filled with a fluid.

17. A device according to claim 16 further comprising an elastic support ring having a support surface for placement against the annular uterine tissue, said hollow ring disposed on said elastic support ring and having a surface for placement against the presenting part of the fetus which is smaller than said support surface of said elastic support ring.

18. A device according to claim 16 wherein said blood flow sensor and said hollow ring are fixed against each other.

19. A device according to claim 16 wherein said hollow ring has a first, flatted side for forming a support on the annular uterine tissue.

20. A device according to claim 19 wherein said first, flattened side of said hollow ring is a rigid material.

21. A device according to claim 10 further comprising electrical contacts adapted to derive the fetal ECG, said electrical contacts provided on one of said blood flow sensor and said pressure sensor.

22. A device according to claim 10 wherein said blood flow sensor is a spiral.

23. A device according to claim 10 wherein said blood flow sensor is a piezofoil.

24. A device for measuring the vital parameters of a fetus inside the uterus of a mother during labor and delivery comprising;

a blood flow sensor for placement on a presenting part of the fetus and adapted to measure blood flow in a presenting part of the fetus;

pressure sensor means for placement between the annular uterine tissue and the presenting part of the fetus, the pressure sensor means for forming an annular occlusion on the presenting part of the fetus.

25. A device according to claim 24, wherein the pressure sensor means is an inflatable hollow ring.

26. A device according to claim 25, wherein the inflatable hollow ring forms a circular shape having an interior portion, and wherein the blood flow sensor is located within the interior portion.

27. A device according to claim 25, wherein the blood flow sensor and the inflatable hollow ring are fixed against each other.

* * * * *